(12) United States Patent
Kilar

(10) Patent No.: US 11,447,730 B2
(45) Date of Patent: Sep. 20, 2022

(54) BIOREACTOR SYSTEM AND METHOD OF BIOPROCESSING

(71) Applicant: GLOBAL LIFE SCIENCES SOLUTIONS USA LLC, Marlborough, MA (US)

(72) Inventor: Alexander Mark Kilar, North Chlemsford, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 765 days.

(21) Appl. No.: 15/992,846

(22) Filed: May 30, 2018

(65) Prior Publication Data
US 2019/0367856 A1   Dec. 5, 2019

(51) Int. Cl.
*C12M 1/00* (2006.01)

(52) U.S. Cl.
CPC ............ *C12M 23/14* (2013.01); *C12M 23/02* (2013.01); *C12M 23/26* (2013.01)

(58) Field of Classification Search
CPC ........ C12M 23/16; C12M 3/04; C12M 3/065; C12M 21/08; C12M 23/06; C12M 29/04; C12M 29/12; C12M 35/08
See application file for complete search history.

(56) References Cited

U.S. PATENT DOCUMENTS

| | | | | |
|---|---|---|---|---|
| 4,539,005 A * | 9/1985 | Greenblatt | .......... | A61M 5/1483 128/DIG. 12 |
| 4,857,055 A * | 8/1989 | Wang | ................ | A61M 5/1483 604/133 |
| 5,096,092 A * | 3/1992 | Devine | ................ | B67D 1/0462 222/105 |
| 5,335,820 A * | 8/1994 | Christianson | ........ | B65D 77/061 222/105 |
| 6,481,598 B1 * | 11/2002 | Thomsen | ............. | B65D 90/048 222/105 |
| 7,377,686 B2 * | 5/2008 | Hubbard | ............... | A61M 1/025 366/208 |
| 7,629,167 B2 | 12/2009 | Hodge et al. | | |
| 7,891,860 B2 * | 2/2011 | Hubbard | ................ | B01F 31/29 366/208 |
| 9,550,157 B2 | 1/2017 | Erdenberger et al. | | |
| 10,106,393 B1 * | 10/2018 | Russell | ............... | B67D 1/0406 |

(Continued)

FOREIGN PATENT DOCUMENTS

| CA | 2801768 | 7/2014 |
|---|---|---|
| WO | 2009/093995 | 7/2009 |

OTHER PUBLICATIONS

International Search Report dated Aug. 9, 2019 from corresponding PCT Application No. PCT/EP2019/063072.

*Primary Examiner* — William H. Beisner
*Assistant Examiner* — Danielle B Henkel
(74) *Attorney, Agent, or Firm* — Gorgan, Tuccillo & Vanderleeden, LLP

(57) ABSTRACT

A bioreactor system includes a vessel having a bottom floor, a flexible bioprocessing bag disposed within the vessel, and a flexible bladder positioned intermediate the bottom floor of the vessel and the bioprocessing bag. The flexible bladder is selectively inflatable to vary at least one of a geometry or configuration of the bioprocessing bag to provide for improved drainability or an increased turndown ratio for the bioreactor system.

16 Claims, 6 Drawing Sheets

(56) References Cited

U.S. PATENT DOCUMENTS

| | | | |
|---|---|---|---|
| 10,632,433 B2* | 4/2020 | Claes | B01F 35/51 |
| 2003/0143727 A1* | 7/2003 | Chang | C12M 23/26 |
| | | | 435/289.1 |
| 2004/0062140 A1* | 4/2004 | Cadogan | B01F 35/513 |
| | | | 366/144 |
| 2008/0130405 A1* | 6/2008 | Hubbard | A61M 1/025 |
| | | | 366/275 |
| 2008/0277428 A1* | 11/2008 | Ingvarsson | B65D 88/62 |
| | | | 222/252 |
| 2009/0188211 A1* | 7/2009 | Galliher | B01F 15/0085 |
| | | | 53/434 |
| 2009/0298180 A1 | 12/2009 | Cattadoris et al. | |
| 2013/0288346 A1 | 10/2013 | Tuohey et al. | |
| 2015/0292994 A1* | 10/2015 | Baril | C12M 41/12 |
| | | | 435/6.12 |
| 2016/0106624 A1* | 4/2016 | Camisani | A61J 1/10 |
| | | | 435/325 |
| 2017/0073624 A1* | 3/2017 | Stankowski | C12M 23/34 |
| 2017/0349874 A1* | 12/2017 | Jaques | C12M 27/02 |

* cited by examiner

BIOREACTOR SYSTEM AND METHOD OF BIOPROCESSING

BACKGROUND

Technical Field

Embodiments of the invention relate generally to bioprocessing systems and methods and, more particularly, to a bioreactor system wherein the shape and/or configuration of a single-use culture bag of such system can be selectively varied.

Discussion of Art

A variety of vessels, devices, components and unit operations are known for carrying out biochemical and/or biological processes and/or manipulating liquids and other products of such processes. Increasingly, in order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

One type of bioreactor mixing system includes a rigid, cylindrical vessel in which a single-use, flexible bag is positioned. The use of sterilized, disposable bags eliminates the time-consuming step of cleaning of the vessel and reduces the chance of contamination. The bag is filled with the desired fluid for mixing and an impeller disposed within the bag (driven by a magnetic drive system or motor positioned outside the vessel) is used to mix the fluid. Depending on the fluid being processed, the system may include a number of fluid lines and different sensors, probes and ports coupled with the bag for monitoring, analytics, sampling, and liquid transfer. For example, a harvest port is typically located at the bottom of the disposable bag and the vessel, and allows for a harvest line to be connected to the bag for harvesting and draining of the bag after the process is complete.

The volume of these single-use, flexible bags typically ranges from about 50 liters to about 2,000 liters. In many applications, such as during the initial stages of scale-up, it is desirable to culture with a working volume that is significantly less than the maximum working volume of the disposable bag. Due to system constraints such as the need to maintain fluid levels within the bag above an area where the sensors penetrate the bag, however, it may sometimes not be possible to work with a volume below a certain lower threshold. This minimum volume at which a given bioreactor system may run effectively, with control, is referred to as the turndown ratio. For example, for many large-scale cell culture applications, before commercial-scale runs can be completed in a 2,000 L bioreactor, processes are first conducted in smaller bioreactors to ensure that cell culture performance scales appropriately and that desired cell density, viability, glycosylation patterns, and expression rates can be realized reproducibly. This process of scaling up can be quite time consuming and costly, requiring the use of a number of different bioreactors of increasing volume. Accordingly, the ability to operate bioreactors at low working volumes (high turn-down ratios) is desirable, as doing so can reduce the number of bioreactors needed for scaling up to a desired harvest volume. Today, most bioreactors have a maximum turndown ratio of 5:1, meaning that a 200 L vessel can operate effectively, with control, down to about 40 L.

While existing bioreactor systems are generally suitable for what can be regarded as ordinary performance, there is a need for a bioreactor system having an increased turndown ratio and improved drainability.

BRIEF DESCRIPTION

In an embodiment, a bioreactor system includes a vessel having a bottom floor, a flexible bioprocessing bag disposed within the vessel, and a flexible bladder positioned intermediate the bottom floor of the vessel and the bioprocessing bag. The flexible bladder is selectively inflatable to vary at least one of a geometry or configuration of the bioprocessing bag.

In another embodiment, a method of bioprocessing includes the steps of disposing a flexible bladder on a bottom floor of a bioreactor vessel, disposing a flexible bioprocessing bag within the vessel generally atop the flexible bladder, carrying out a bioprocess within the flexible bioprocessing bag, and inflating the flexible bladder to vary at least one of a geometry or configuration of the flexible bioprocessing bag.

In yet another embodiment, an apparatus for use in a bioreactor system includes a flexible bladder having an inlet port configured for connection to a supply of pressurized air. The flexible bladder is configured to be positioned on a bottom floor of a bioreactor vessel beneath a flexible bioprocessing bag also disposed within the vessel, and is configured to be selectively inflated with the supply of pressurized air to vary a geometry or configuration of the flexible processing bag to improve drainability or increase turndown ratio of the bioreactor system.

DRAWINGS

The present invention will be better understood from reading the following description of non-limiting embodiments, with reference to the attached drawings, wherein below:

DETAILED DESCRIPTION

Figure 1:
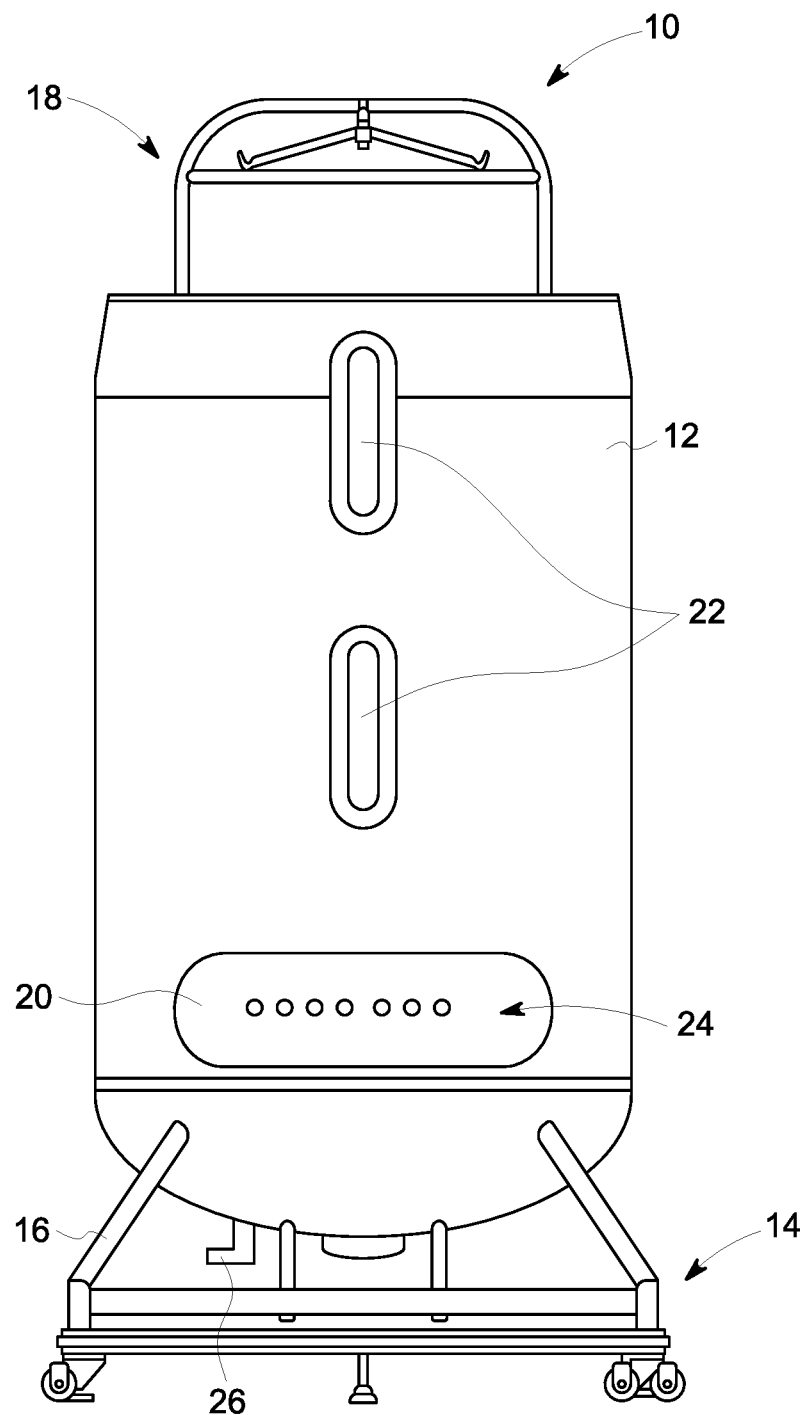
FIG. 1 is a front elevational view of a bioreactor system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container or vessel used, for example, as a bioreactor or mixer for the contents within.

As used herein, the term "turndown ratio" refers to the width of the operational range of a bioreactor, and is defined as the ratio of the maximum operating volume to the minimum operating volume of the bioreactor. For example, a bioreactor with a maximum operating volume of 200 liters and a minimum operating volume of 40 liters has a turndown ratio of 5:1. As used herein, "drainability" refers to the ability to easily and completely drain the contents of the bioreactor during drain-down or harvest of a batch.

Embodiments of the invention provide a bioreactor system having a vessel having a bottom floor, a flexible bioprocessing bag disposed within the vessel, and a flexible bladder positioned intermediate the bottom floor of the vessel and the bioprocessing bag. The flexible bladder is selectively inflatable to vary at least one of a geometry or configuration of the bioprocessing bag to provide for improved drainability or an increased turndown ratio for the bioreactor system.

Figure 2:
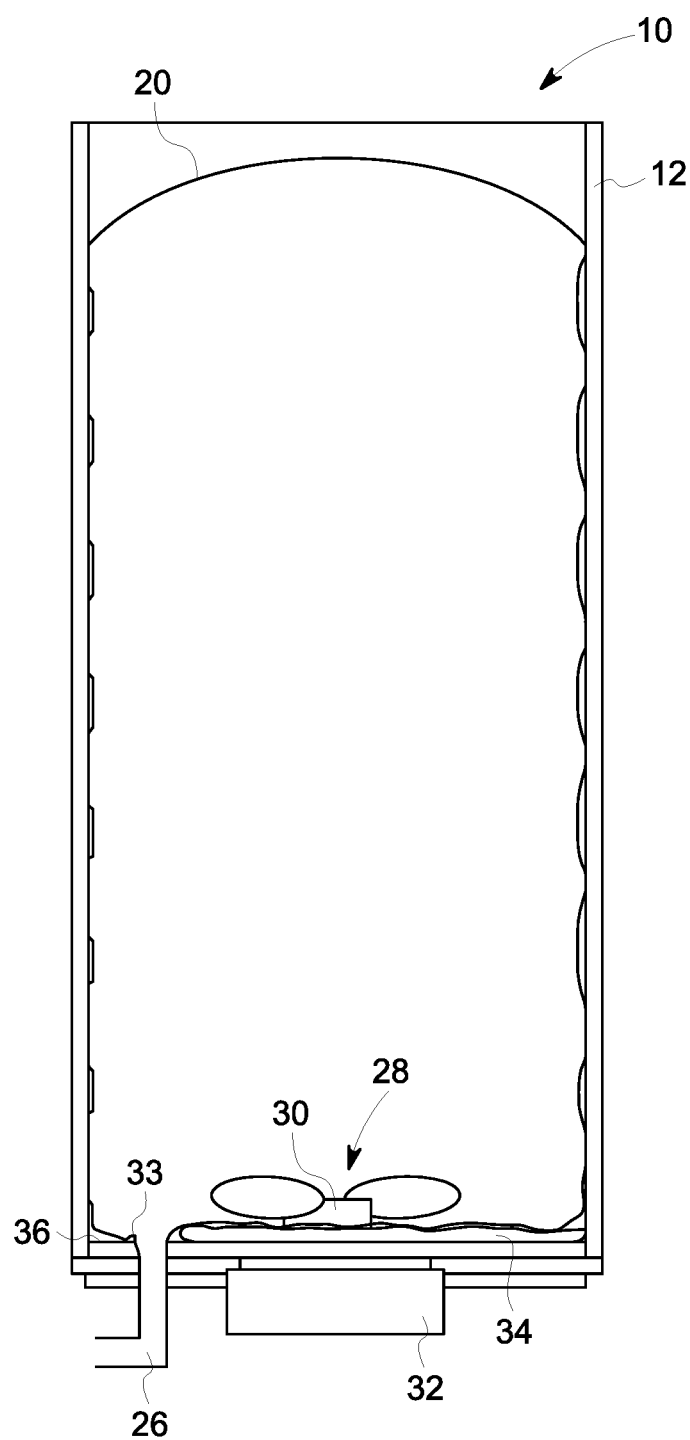
FIG. 2 is a simplified side elevational, cross-sectional view of the bioreactor system of FIG. 1, with a single-use, flexible bag and inflatable bladder disposed therein, and showing the bladder in an uninflated state.

With reference to FIGS. 1 and 2, a bioreactor system 10 according to an embodiment of the invention is illustrated. The bioreactor system 10 includes a generally rigid bioreactor vessel or support structure 12 mounted atop a base 14 having a plurality of legs 16. The vessel 12 may be formed, for example, from stainless steel, polymers, composites, glass, or other metals, and may be cylindrical in shape, although other shapes may also be utilized without departing from the broader aspects of the invention. The vessel 12 may be outfitted with a lift assembly 18 that provides support to a single-use, flexible bag 20 disposed within the vessel 12. The vessel 12 may include one or more sight windows 22, which allows one to view a fluid level within the flexible bag 20, as well as a window 24 positioned at a lower area of the vessel 12. The window 24 allows access to the interior of the vessel 12 for insertion and positioning of various sensors and probes (not shown) within the flexible bag 20, and for connecting one or more fluid lines to the flexible bag 20 for fluids, gases, and the like, to be added or withdrawn from the flexible bag 20. Sensors/probes and controls for monitoring and controlling important process parameters include any one or more, and combinations of: temperature, pressure, pH, dissolved oxygen (DO), dissolved carbon dioxide ($pCO_2$), mixing rate, and gas flow rate, for example. As shown in FIG. 1, the vessel 12 may also include a discharge port 26 in the bottom surface thereof, to which discharge tubing may be connected, for draining and/or harvesting the contents of the flexible bag 20.

With specific reference to FIG. 2, a schematic side elevational, cutaway view of the bioreactor system 10 is illustrated. As shown therein, the single-use, flexible bag 20 is disposed within the vessel 10 and restrained thereby. The flexible bag 20 contains an impeller 28 attached to a magnetic hub 30 at the bottom center of the inside of the bag, which rotates on an impeller plate (not shown) also positioned on the inside bottom of the bag 20. A magnetic drive 32 external to the vessel 12 provides the motive force for rotating the magnetic hub 30 to mix the contents of the flexible bag 20. While FIG. 2 illustrates the use of a magnetically-driven impeller, other types of impellers and drive systems are also possible, including top-driven impellers. The single-use, flexible bag 20 further includes an outlet port 33 that is configured to be aligned with, and coupled, to the discharge port 26, providing fluid communication therewith for draining of the bag 20 after processing, as needed and desired.

Figure 3:
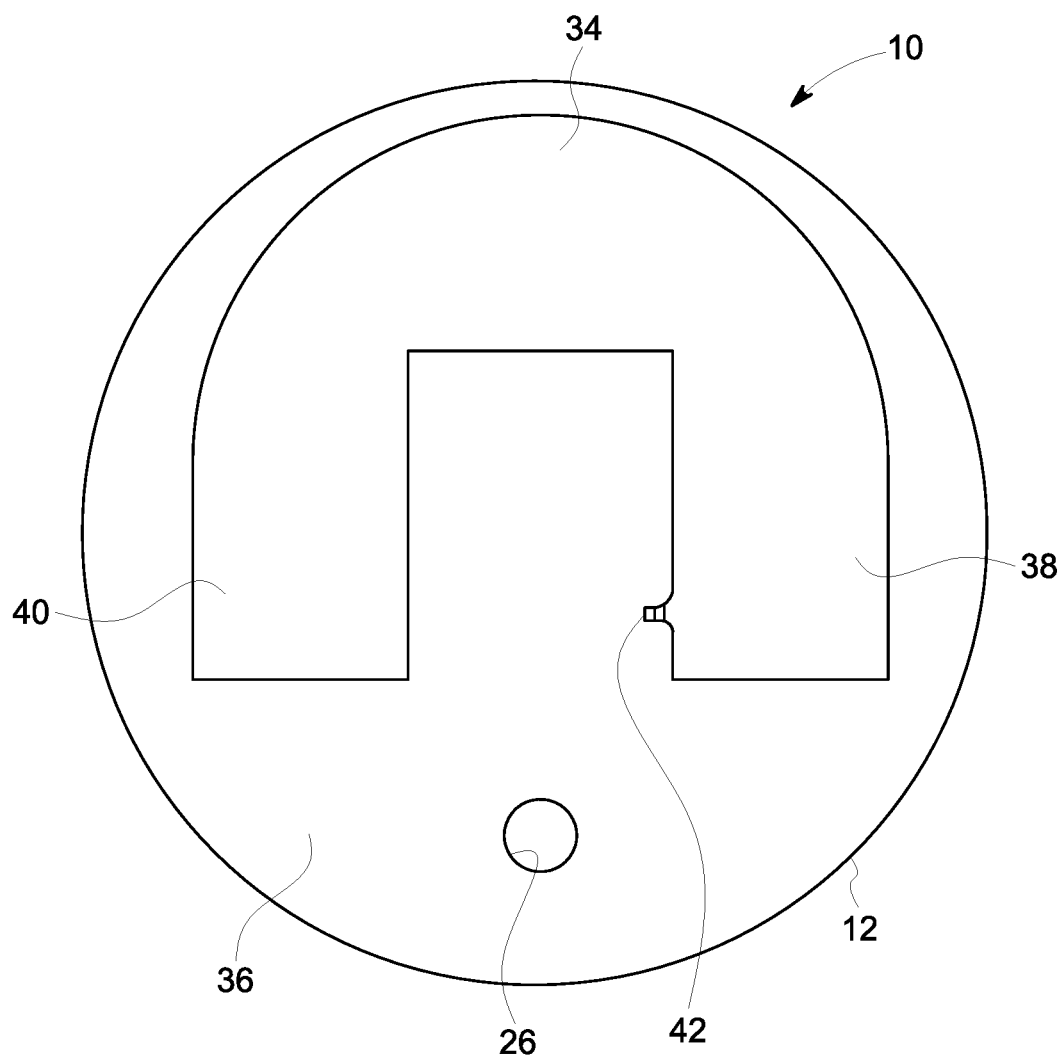
FIG. 3 is a simplified, top plan view of the bioreactor system of FIG. 1, with the inflatable bladder disposed therein.
Figure 4:
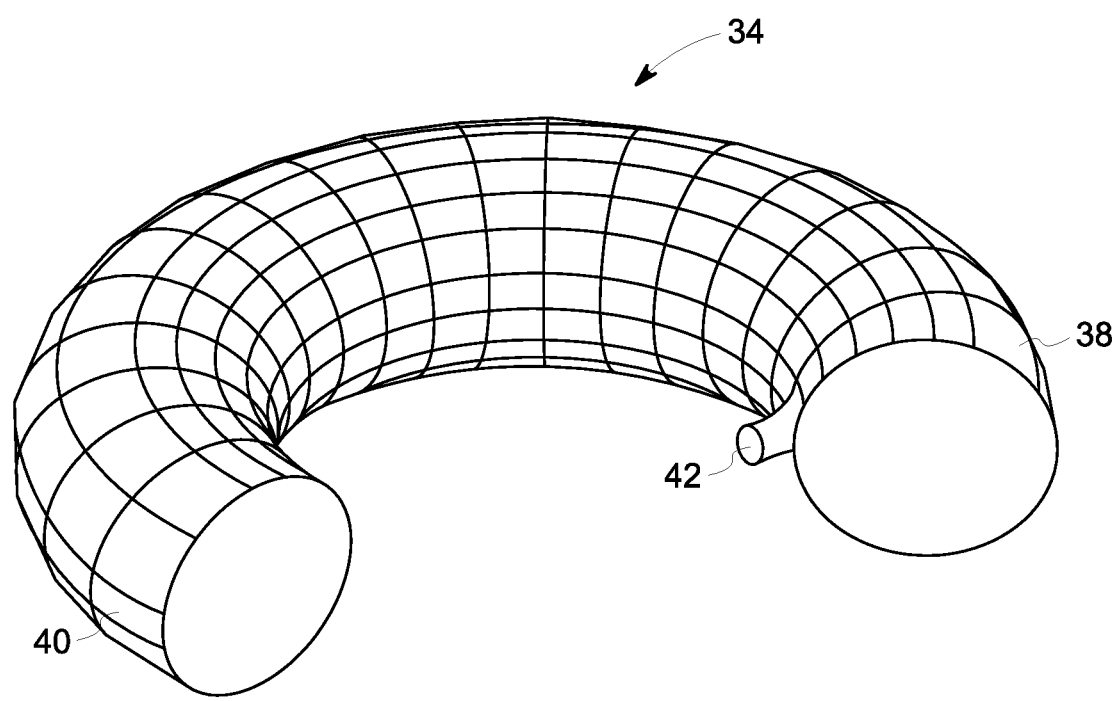
FIG. 4 is a perspective view of the inflatable bladder, according to an embodiment of the invention.

As shown in FIGS. 2 and 3, the bioreactor system 10 also includes an inflatable bladder 34 that rests on the bottom surface or floor 36 of the vessel 12 beneath the flexible bag 20. In particular, the bladder 34 is positioned intermediate the bottom floor 36 of the vessel 12 and the bottom of the flexible bag 20. As illustrated in FIG. 3, the inflatable bladder 34 is generally U-shaped and has a pair of opposed leg portions 38, 40 that extend generally toward the discharge port 26 in the vessel 12. An inflation port 42 is provided in one of the legs 38, 40 for selectively inflating and deflating the inflatable bladder 34, as discussed hereinafter, although the inflation port may be located elsewhere on the bladder without departing from the broader aspects of the invention. FIG. 4 provides a more detailed illustration of the inflatable bladder 34. As shown therein, the inflatable bladder 34 may take the shape of a segmented torus, and has a peripheral shape that generally corresponds to the peripheral shape of the vessel 12 and bag 20.

Figure 5:
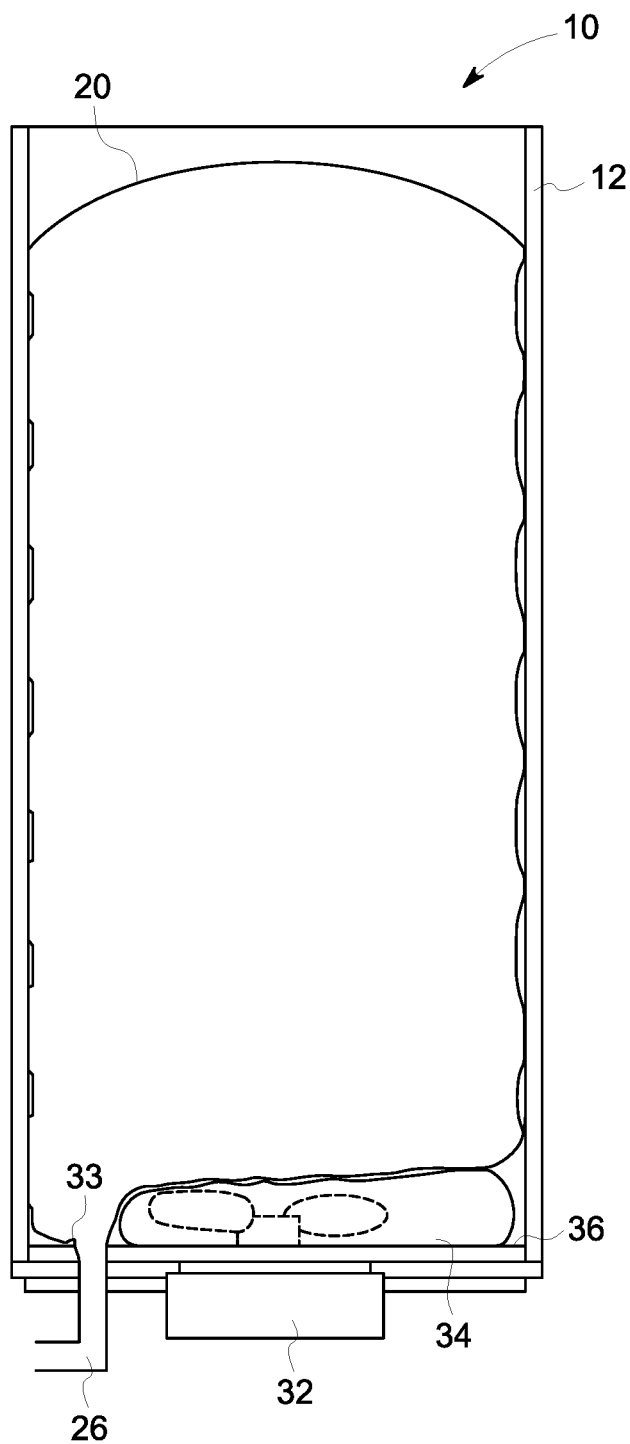
FIG. 5 is a simplified side elevational, cross-sectional view of the bioreactor system of FIG. 1, with a single-use, flexible bag and inflatable bladder disposed therein, and showing the bladder in an inflated state.

As discussed in detail hereinafter, the bladder 34 is selectively inflatable and deflatable to vary the shape, geometry and volume of the flexible bag 20 (and, particularly, the shape and geometry of the bottom of the flexible bag 20) that sits atop the bladder 34. FIG. 2 illustrates the bladder 34 in its deflated state, while FIG. 5 illustrates the bladder 34 in its fully inflated state. In an embodiment, the bladder 34 may be inflated to any intermediate state between the deflated state and the inflated state, as discussed hereinafter.

In embodiments, the single-use, flexible bag 20 is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra-low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. Portions of the flexible container can comprise a substantially rigid material such as a rigid polymer, for example, high density polyethylene, metal, or glass. In an embodiment, the inflatable bladder 34 may be formed from a flexible material that is the same as, or different from, the single-use, flexible bag 20.

Figure 6:
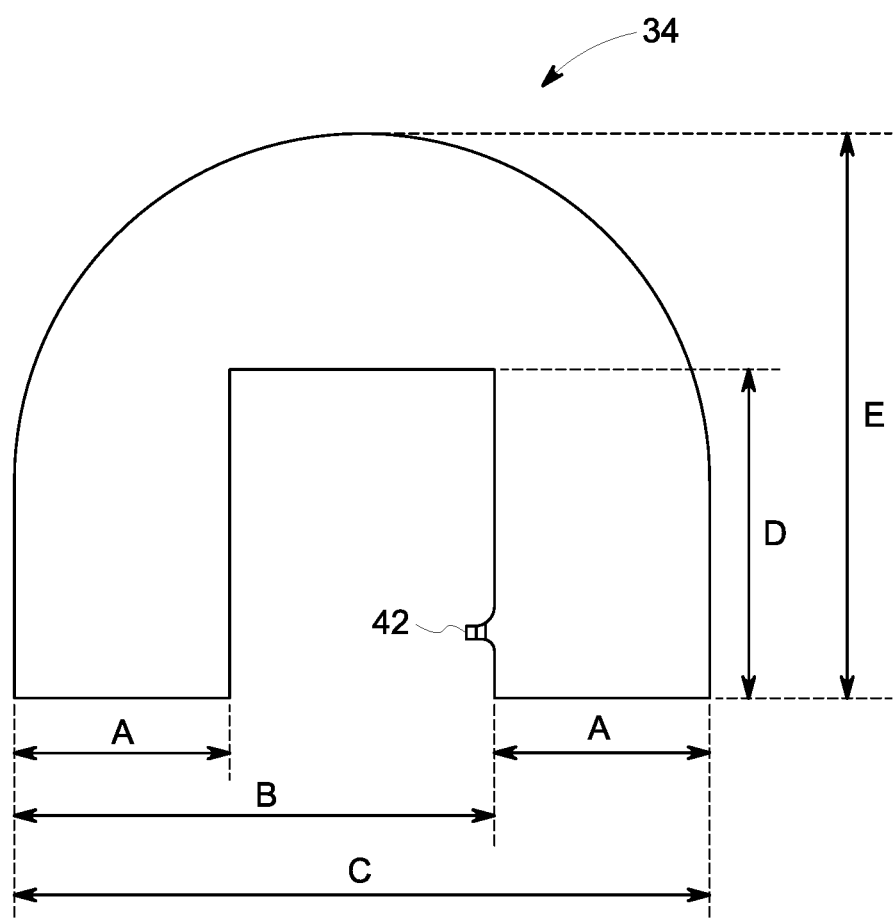
FIG. 6 is a top plan view of the inflatable bladder according to an embodiment of the invention, showing dimensional relationships of the bladder.

FIG. 6 is a top plan view of an exemplary bladder 34, showing various dimensional relationships of the bladder. For a bioreactor and disposable bag having a maximum working volume of about 200 liters such as, for example, General Electric's XDR-200 single-use, stirred-tank bioreactor, which has an inner diameter of about 22 inches, the bladder 34 may having the configuration shown in FIG. 6, where A is approximately 4 inches, B is approximately 15¾ inches, C is approximately 19¾ inches, D is approximately 5 inches and E is approximately 11½ inches. Other dimensional relationships and bladder configurations are also possible. As discussed in detail below, the inflatable bladder may be sized to allow the bioreactor system to run at almost any fluid volume desired. In particular, the volume of the bladder 34 can be chosen so that in an inflated state, a level of the fluid within the flexible bag 20 is above a point where the sensors penetrate the flexible bag 20. In addition, a shape of the bladder 34 may be chosen so as to surround, but not interfere with, operation of the impeller (where either a top-mounted or bottom-mounted impeller is utilized).

In use, the inflatable bladder 34 may be positioned at the bottom of the vessel 12 prior to insertion of the single-use, flexible bag into the vessel 12. The inflation port 42 of the inflatable bladder 34 may then be connected to a supply of instrument air through a hose extending through the drain port in the vessel 12 or through the bottom opening in the vessel 12 through which the magnetic drive for the impeller extends. In an embodiment, the instrument air is capable of providing 30-90 psi for inflation. The single-use, flexible bag 20 is then positioned atop the bladder 34 (in its deflated state), and the outlet port 33 in the bag 20 is connected to the discharge port 36 of the vessel 12, and the impeller 28 is coupled to the magnetic drive 32, in a manner heretofore known in the art.

In one mode of operation, a bioprocessing operation is carried out within the bag in a conventional manner. After processing, such as during a harvest step, or at any time where draining of the bag is necessary, the contents of the bag 20 may be released through the discharge port 36. During draining or harvesting, as the fluid level in the bag 20 decreases, the bladder 34 may be inflated using the supply of instrument air. As illustrated in FIG. 5, when the bladder 34 is inflated, it raises the flexible bag 20 upwards in the areas where it contacts the bag 20. Where the bladder 34 is in the shape of a segmented torus, it pushes the bag 20 upwards along the bottom, outer periphery of the bag 20. Inflating the bladder 34 therefore varies the configuration and shape of the bottom of the flexible bag 20, creating a funnel-like configuration in the bottom of the bag 20. This functions to facilitate draining of the bag, particularly during the last stages of drain-down, as the funnel-like shape causes the fluid within the bag 20 to flow towards the outlet port 33 and drain port 26. This is in contrast to existing systems where the flexible bag sits generally flat on the bottom of the vessel during the entire draining process, resulting in less than full draining and/or very slow draining as the fluid level decreases.

In another mode of operation, the inflatable bladder 34 may be utilized to increase and improve the turndown ratio. For example, once the bladder 34 and flexible bag 20 are positioned in the vessel 12 in the manner hereinbefore described, the bladder may be inflated to lift at least a portion of the bag 20 off of the bottom of the vessel 12. In an embodiment, process media may be added to the bag 20 either before or after inflation of the bladder 34. Inflating the bladder 34 effectively decreases the volume of the bag, and raises the fluid level within the bag 20 as compared to when the bag 20 is sitting fully on the bottom of the vessel 12. With the bladder 34 in its inflated state, with process media in the bag 20, bioprocessing may then commence and be carried out in the conventional manner. As the process is expanded out and the fluid level within the bag increases, the bladder 34 may be deflated (at once or in stages) so that the maximum working volume of the bag 20 can be utilized. In particular, the bladder 34 may be progressively (or essentially instantaneously) deflated as the batch is expanded.

By inflating the bladder 34 during the initial stages of processing, an improved turndown ratio for the bioreactor system may be achieved. For example, a conventional 200 liter bioreactor, using a 200 liter disposable bag, may have a minimum operating volume of 40 liters, equating to a turndown ratio of 5:1. This means that at the minimum operating volume of 40 liters, the fluid level within the bag will be above the sensors, allowing for desired process control. With less than 40 liters in the bag, however, the level of fluid in the bag may decrease to a point where accurate sensor readings cannot be obtained (if at all). Accordingly, in such a conventional system, the process cannot be run effectively at volumes below 40 liters.

By using the inflatable bladder 34 described herein, which may have, for example, an internal volume in its inflated state of 10-15 liters, the minimum operating volume of the bioreactor may be pushed down to about 25-30 liters. In particular, inflation of the bladder 34 can be utilized to maintain a minimum fluid level within the bag (e.g., at a level above the sensors) for bioprocessing operations to be carried out at lower fluid volumes than would otherwise be necessary if the bag extended all the way to the bottom of the vessel. For example, with the 200 liter bioreactor described above, if the volume of the fluid is, e.g., 25-30 liters, the level of fluid may be below the level required for accurate sensing of process conditions and parameters. Inflation of the bladder 34, however, will displace the fluid upward, pushing the fluid level above the level required for accurate sensing, thereby enabling the bioreactor to run at a lower fluid volume. Accordingly, in the example described above where inflation of the bladder 34 allows the minimum operating volume to be decreased from 40 liters to about 25-30 liters, the turndown ratio of the bioreactor system may be increased to about 6:1 to 8:1, or more.

While the bladder 34 is shown and described herein as having the shape of a segmented torus, the invention is not so limited in this regard. Indeed, the shape or configuration of bladder may be selected to provide any fluid flow configuration desired during draining or harvesting, in dependence upon one or more of the configuration or shape of the flexible bag, the configuration or shape of the vessel and/or the bottom floor thereof, and the location of the drain port and/or impeller/drive components. For example, the bladder 34 may be torus, annular shaped, or wedge shaped, although other shapes and configurations such as rectangular, triangular or the like are also possible without departing from the broader aspects of the invention. In an embodiment, the peripheral shape of the bladder may selected to correspond or mirror the interior peripheral shape (defined by the interior sidewalls) of the vessel. In addition, the volume of the bladder 34 may be selected to facilitate draining or to increase turndown ratio to a desired degree, as described above.

While the inflatable bladder has been shown and described herein for use with a generally cylindrical, flat bottom bioreactor vessel various modifications may be made to enable use of the bladder with bioreactors having other configurations. For example, it is intended that the size, shape and configuration of the bladder may be selected so as to enable use of the bladder with vessels of any shape (including square, rectangular, etc.), any bottom configuration (flat or funnel-shaped), and with any impeller configuration (top-mounted or bottom-mounted).

In an embodiment, rather than being a separate component that is oriented within the vessel 12 prior to positioning of the single-use, flexible bag 20 within the vessel, the bladder 34 may be integrated with the bag 20 itself. For example, the bladder 34 may be welded to the bottom of the bag 20 such that the bag 20 will contain two separate compartments, one in the form of an inflatable bladder, and the other for holding process media and carrying out a bioprocessing operation. The integrated bag and bladder may be utilized in situations where ease of installation is desired, as both the bladder and processing compartment can be installed in the vessel in a single step. Where cost savings are of primary concern, a separate bladder and bag may be utilized so that after drain-down and harvesting, the inflatable bladder may be reused.

As discussed above, the flexible bladder of the invention therefore provides for improved drainability for the bioreactor system, as well as allows for the turndown ratio of the system to be increased by providing the ability to selectively raise the fluid level within the flexible bag to a level above the sensors upon inflation of the bladder. Moreover, the ability to precisely control the level of inflation and deflation allows for precise control over the manufacturing process, to an extent heretofore not seen in the art.

In an embodiment, a bioreactor system is provided. The bioreactor system includes a vessel having a bottom floor, a flexible bioprocessing bag disposed within the vessel, and a flexible bladder positioned intermediate the bottom floor of the vessel and the bioprocessing bag. The flexible bladder is selectively inflatable to vary at least one of a geometry or configuration of the bioprocessing bag. In an embodiment, the vessel includes a drain port in the floor, and bioprocessing bag includes an outlet port configured for connection with the drain port, wherein the outlet port and the drain port cooperating to facilitate draining of the contents of the bioprocessing bag. In an embodiment, the bladder is selectively inflatable to elevate at least a portion of the bioprocessing bag above a level of the outlet port. In an embodiment, the bladder is selectively inflatable to create a funnel-like shape at the bottom of the bioprocessing bag to funnel contents of the bioprocessing bag towards the outlet port. In an embodiment, the bladder has a torus or segmented torus shape in an inflated state. In another embodiment, the bladder has a wedge shape in an inflated state. In an embodiment, the flexible bladder is shaped and positioned so as to generally surround the drain port in the bottom floor of the vessel. In an embodiment, the bladder is integrated with the bioprocessing bag. In an embodiment, the vessel is substantially rigid.

In another embodiment, a method of bioprocessing is provided. The method includes the steps of disposing a flexible bladder on a bottom floor of a bioreactor vessel, disposing a flexible bioprocessing bag within the vessel generally atop the flexible bladder, carrying out a bioprocess within the flexible bioprocessing bag, and inflating the flexible bladder to vary at least one of a geometry or configuration of the flexible bioprocessing bag. In an embodiment, the method also includes the step of connecting the flexible bladder to a supply of pressurized air. The step of connecting the flexible bladder to the supply of pressurized air may include inserting a hose from the supply of pressurized through a drain port in the bottom of the vessel and connecting the hose to an inlet port of the flexible bladder. In an embodiment, the step of inflating the flexible bladder is carried out during draining of the flexible bioprocessing bag. In an embodiment, the method may also include the step of positioning the flexible bladder to at least partially surround a drain port in the bottom floor of the vessel. In an embodiment, the step of inflating the flexible bladder is carried out during a first stage of the bioprocess, and the method may also include the step of deflating the flexible bladder during a second stage of the bioprocess, the second stage occurring temporally after the first stage. In an embodiment, the step of inflating the flexible bladder is carried out prior to carrying out the bioprocess within the flexible bioprocessing bag, and the method may also include steps of, expanding a culture within the flexible bioprocessing bag, whereby expanding the culture increases a fluid level within the flexible bioprocessing bag, and deflating the flexible bladder as the fluid level within the flexible bioprocessing bag increases. In an embodiment, the flexible bladder has one of an annular, segmented torus or wedge shape in an inflated state. In an embodiment, the flexible bladder is integrated with the flexible bioprocessing bag.

In yet another embodiment, an apparatus for use in a bioreactor system is provided. The apparatus includes a flexible bladder having an inlet port configured for connection to a supply of pressurized air. The bladder is configured to be positioned on a bottom floor of a bioreactor vessel beneath a flexible bioprocessing bag also disposed within the vessel, and to be selectively inflated with the supply of pressurized air to vary a geometry or configuration of the flexible processing bag to improve drainability or increase turndown ratio of the bioreactor system. In an embodiment, the flexible bladder has one of an annular, segmented torus or wedge shape in an inflated state.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:
1. A bioreactor system, comprising:
a vessel having a bottom floor;
a flexible bioprocessing bag disposed within the vessel; and a flexible bladder positioned intermediate the bottom floor of the vessel and the bioprocessing bag, and entirely beneath the bioprocessing bag;
wherein the flexible bladder is selectively inflatable to vary at least one of a geometry or configuration of the bioprocessing bag;
wherein the flexible bladder has a torus or segmented torus shape in an inflated state;
wherein the inflated torus or segmented torus creates a funnel shape at a bottom of the bioprocessing bag to funnel contents of the bioprocessing bag towards the bottom floor of the vessel.

2. The bioreactor system of claim 1, wherein:
the vessel includes a drain port in the bottom floor of the vessel;
wherein the bioprocessing bag includes an outlet port configured for connection with the drain port, the outlet port and the drain port cooperating to facilitate draining of the contents of the bioprocessing bag.

3. The bioreactor system of claim 2, wherein:
the flexible bladder is selectively inflatable to elevate at least a portion of the bioprocessing bag above a level of the outlet port.

4. The bioreactor system of claim 3, wherein:
the funnel shape directs the contents of the bioprocessing bag towards the outlet port.

5. The bioreactor system of claim 4, wherein:
the flexible bladder is shaped and positioned so as to generally surround the drain port in the bottom floor of the vessel.

6. The bioreactor system of claim 1, wherein:
the flexible bladder is integrated with the bioprocessing bag.

7. The bioreactor system of claim 1, wherein:
the vessel is substantially rigid.

8. A method of bioprocessing, comprising the steps of:
disposing a flexible bladder on a bottom floor of a bioreactor vessel;
disposing a flexible bioprocessing bag within the vessel generally atop the flexible bladder;
carrying out a bioprocess within the flexible bioprocessing bag; and
inflating the flexible bladder to a torus or segmented torus shape during draining of the flexible bioprocessing bag to create a funnel shape in a bottom of the flexible bioprocessing bag to funnel contents of the flexible bioprocessing bag towards a drain port in the bottom floor of the bioreactor vessel.

9. The method of bioprocessing of claim 8, further comprising the step of:
connecting the flexible bladder to a supply of pressurized air.

10. The method of bioprocessing of claim 9, further comprising the step of:
positioning the flexible bladder to at least partially surround a drain port in the bottom floor of the vessel.

11. The method of bioprocessing of claim 9, wherein:
the step of inflating the flexible bladder is carried out during a first stage of the bioprocess; and
wherein the method further includes the step of deflating the flexible bladder during a second stage of the bioprocess, the second stage occurring temporally after the first stage.

12. The method of bioprocessing of 11, wherein:
the step of inflating the flexible bladder is carried out prior to carrying out the bioprocess within the flexible bioprocessing bag; and
wherein the method further includes the steps of:
expanding a culture within the flexible bioprocessing bag, whereby expanding the culture increases a fluid level within the flexible bioprocessing bag; and
deflating the flexible bladder as the fluid level within the flexible bioprocessing bag increases.

13. The method of bioprocessing of claim 8, wherein:
the flexible bladder is integrated with the flexible bioprocessing bag.

14. The method of bioprocessing of claim 9, wherein:
the step of connecting the flexible bladder to the supply of pressurized air includes inserting a hose from the supply of pressurized air through the drain port in the bottom floor of the bioreactor vessel and connecting the hose to an inlet port of the flexible bladder.

15. A method of bioprocessing, comprising the steps of:
disposing a flexible bladder on a bottom floor of a bioreactor vessel;
disposing a flexible bioprocessing bag within the bioreactor vessel generally atop the flexible bladder, wherein the flexible bioprocessing bag includes a maximum operating volume that can be used to perform a bioprocessing operation in the flexible bioprocessing bag and a minimum operating volume that can be used to perform the bioprocessing operation, wherein the minimum operating volume has a minimum fluid level or height associated therewith that is indicative of an amount of fluid that is necessary for one or more sensors operatively coupled to the flexible bioprocessing bag to obtain accurate measurements from the fluid in the flexible bioprocessing bag for process control of the bioprocessing operation;
filling the flexible bioprocessing bag with the fluid;
inflating the flexible bladder to an inflated state causing the fluid within the flexible bioprocessing bag to exceed the minimum fluid level or height for performing the bioprocessing operation, whereby in a deflated state of the flexible bladder the level of fluid within the flexible bioprocessing bag is below the minimum fluid level or height;
carrying out the bioprocessing operation within the flexible bioprocessing bag with the flexible bladder in the inflated state, wherein the bioprocessing operation includes expanding a culture within the flexible bioprocessing bag, and wherein the fluid level or height increases during culture expansion; and
deflating the flexible bladder as the fluid level or height within the flexible bioprocessing bag increases for utilization of the maximum operating volume as the culture expansion proceeds.

16. The method according to claim 15, further comprising the steps of:
adding additional fluid to the flexible bioprocessing bag to increase the level of fluid within the flexible bioprocessing bag after deflating the flexible bladder; and
deflating the flexible bladder in response to determining that is no further need to maintain the level of fluid above the minimum fluid level or height for the bioprocessing operation.

* * * * *